US00PP26285P2

(12) United States Plant Patent
Kordes

(10) Patent No.: US PP26,285 P2
(45) Date of Patent: Jan. 5, 2016

(54) HYBRID TEA ROSE PLANT NAMED 'KORVIOROS'

(50) Latin Name: *Rosa hybrida*
Varietal Denomination: KORvioros

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 127 days.

(21) Appl. No.: 13/998,343

(22) Filed: Oct. 22, 2013

(51) Int. Cl.
*A01H 5/02* (2006.01)

(52) U.S. Cl.
USPC ..... Plt./137

(58) Field of Classification Search
USPC ..... Plt./137
See application file for complete search history.

*Primary Examiner* — Keith Robinson

(57) ABSTRACT

A new and distinct variety of rose with long lasting, fragrant, novel soft pink flowers, and attractive foliage with excellent disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORvioros'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1999. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORvioros'.

SUMMARY OF THE INVENTION

The new rose plant may be distinguished from its seed parent, an 'un-named seedling', by the following combination of characteristics:

1. 'KORvioros' has soft pink flowers, whereas the 'un-named seedling' has salmon pink flowers.
2. 'KORvioros' has a flattened flower shape, whereas the 'un-named seedling' has a cupped flower shape.

The new rose plant may be distinguished from its pollen parent, an 'un-named seedling', by the following combination of characteristics:

1. 'KORvioros' has a very double petal count, whereas the 'un-named seedling' has a double petal count.
2. 'KORvioros' has a vigorous growth habit, whereas the 'un-named seedling' has a moderate growth habit.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORvioros' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORvioros' was selected in May 2000 from the seedling beds to be asexually propagated for further evaluation. The first asexual propagation of 'KORvioros' was done by budding in July 2000 at the inventor's nursery in Offenseth-Sparrieshoop, Germany.

These initial and other subsequent propagations conducted in controlled environments demonstrate that 'KORvioros' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORvioros' taken from a 2 year old plant.

DETAILED BOTANICAL DESCRIPTION

The following is a description of 'KORvioros', as observed growing in September 2013 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORsteflali', a rose variety from the same inventor described and illustrated in U.S. Plant Pat. No. 23,570 and issued on Apr. 30, 2013 are compared to 'KORvioros' in Chart 1.

CHART 1

| Characteristic | 'KORvioros' | 'KORsteflali' |
|---|---|---|
| Petal count | 155-160 | 40-50 |
| Flower fragrance | Strong | Moderate |
| Stamen count | 0-5 | 30 |

Parents:

*Seed parent*.—An 'un-named seedling'.

*Pollen parent*.—An 'un-named seedling'.

Classification:

*Botanical classification*.—*Rosa hybrida* 'KORvioros'.

*Commercial classification*.—Hybrid Tea rose.

FLOWER AND FLOWER BUD

*Blooming habit*.—Recurrent.

*Flower bud*.—Size: Upon opening, 20-22 mm in length from base of receptacle to distal end of bud and 17-18 mm diameter at its widest point. Bud form: Short. Pointed ovoid. Bud color: As sepals first unfold, bud color is Greyed-Orange Group N170C. When ¼ open, the upper surface of petals is Red Group 48D, and the lower surface is Red Group 49C. Guard Petals are Red Group 49C with intonations of Red-Purple Group 59C and Red-Purple Group 59D.

*But texture*.—Smooth. Sepals: Color: Upper surface Yellow-Green Group 144A. Lower surface Yellow-Green Group 144B. Size: Average 20-25 mm (l)×8-10 mm (w). Shape: Moderate foliaceous appendages on 3 of the five sepals. Apex: Cirrose. Base: Flat at union with receptacle. Quantity: Five. Surface texture: Upper side: Pubescent. Lower surface: Smooth. Stipitate glands: Limited numbers along margins.

*Flower bloom*.—Fragrance: Strong. Duration: On the plant 6-7 days. Senesced petals drop away cleanly. Size: Large for a hybrid tea rose. When open, the average flower diameter is 100 mm and the average flower height is 35 mm. Form: Shape of flower when viewed from the side: Upon opening, upper part: Convex. Upon opening, lower part: Concave. Open flower, upper part: Flattened convex. Open flower, lower part: Concave.

*Color*.—Upon opening, petals: Outermost petals: Outer Side: White Group N155B with Red-Purple Group 62C and Red-Purple Group 62D along the margins. Inner Side: Red-Purple Group 62C with Red-Purple Group 62C along the margins. Innermost petals: Outer Side: Red Group 49C. Inner Side: Red Group 49B. Upon opening, basal petal spots: Basal petal spot, outermost petals: Outer Side: No distinctive coloration at petal base observed. Inner Side: Green-Yellow Group 1D. Basal petal spot, innermost petals: Outer Side: No distinctive coloration at petal base observed. Inner Side: Yellow Group 2B. After opening, petals: Outermost petals: Outer Side: White Group N155B with Red-Purple Group 62B, Red-Purple Group 62C and Red-Purple Group 62D along the margins. Inner Side: White Group N155B with Red-Purple Group 62B, Red-Purple Group 62C and Red-Purple Group 62D along the margins. Innermost petals: Outer Side: Red Group 56C. Inner Side: Red Group 55D. After opening, basal petal spots: Basal petal spot, outermost petals: Outer Side: No distinctive coloration at petal base observed. Inner Side: Green-Yellow Group 1D. Basal petal spot, innermost petals: Outer Side: No distinctive coloration at petal base observed. Inner Side: Yellow Group 2D.

General tonality: On open flower Red Group 49B. No change in the general tonality at the end of the 6$^{th}$ day. Afterwards, general tonality is Red Group 49D.

Petals:

*Flower type*.—Very Double.

*Petal count*.—Approximately 155-160 petals under normal conditions.

*Petal reflex*.—Petals reflex slightly.

*Petal margin*.—Entire.

*Petal shape*.—Obovate. Apex: Obtuse. Base: Cuneate.

*Petal size*.—25-50 mm (l)×15-40 mm (w).

*Thickness*.—Average.

*Petal arrangement*.—Not formal.

*Texture*.—Upper: Smooth. Lower: Smooth.

Petaloids:

*Petaloid count*.—Average of 5-10 per flower.

*Petaloid size*.—10-12 mm (l)×7-8 mm (w).

*Petaloid color*.—Inner side: Red Group 43D. Outer side: Red Group 43D.

*Petaloid texture*.—Upper: Smooth. Lower: Smooth.

*Margins*.—Entire. Petaloid Shape: Most commonly obovate with some petaloids highly irregular. Apex: Obtuse. Base: Cuneate.

Reproductive organs:

*Ovary*.—Color: Green-While Group 157C. Length: 4-7 mm. Diameter: 5-6 mm.

*Pistils*.—Few. Approximately 30-35 present. Stigmas: Location: Superior in position to anthers. Color: Greyed-Yellow Group 161A. Styles: Length: About 10 mm long. Color: Green-White Group 157C with intonations of Red-Purple Group 58A.

*Stamens*.—Approximately 0-5 on average and regularly arranged. Anthers: Size: Average 3 mm (l)×2 mm (w). Color: Greyed-Yellow Group 161D. Pollen: Limited. Pollen Color: Yellow-Orange Group 20B. Filaments: Color: Yellow Group 9A. Length: 2-3 mm.

*Receptacle*.—Surface: Glabrous. Color: Yellow-Green Group 144A with intonations of Greyed-Purple Group 184A. Shape: Funnel-shaped. Texture: Smooth. Size: 7-8 mm (h)×8-10 mm (w).

*Peduncle*.—Length: 45-55 mm average length. Diameter: 3-4 mm average diameter. Color: Yellow-Green Group 144A with intonations of Greyed-Purple Group 184A. Strength: Strong. Texture: Glabrous. Borne: Singularly.

THE PLANT

*Growth*.—Vigorous.

*Plant habit*.—Upright to bushy. When grown as a field plant, the average plant height is 137 cm and the average plant width is 122 cm.

*Stems*.—Stem color: Young wood: Yellow-Green Group 144A. Older wood: Green Group 138A. Intonations: Greyed-Purple Group 187B on 90-95% of young wood and 80% of old wood. Stem surface texture: Young wood: Smooth. Older wood: Rough.

*Prickles*.—Present. Incidence: Average of 9 per each 10 cm of stem. Size: Average length: 5-7 mm. Color: Immature prickles: Greyed-Purple Group 187C. Mature prickles: Greyed-Brown Group N199D. Senescing to Greyed-Orange Group 164C. Shape: Deeply concave. Texture: Smooth. Anthocyanin: Greyed-Purple Group 187B.

*Leaves*.—Normally 5-7 leaflets on normal leaves in middle of the stem. Venation pattern: Pyramidal net pattern. Leaf size: 140 mm (l)×115 mm (w). Abundance: Very abundant. Surface: Upper: Semi-glossy to Glossy. Lower: Matte. Shape: Elliptic. Base: Obtuse. Apex: Acute. Margins: Serrated. Texture: Upper Leaf Surface: Leathery. Lower Leaf Surface: Rugose. Color, mature foliage: Upper Leaf Surface: Green Group 139A. Lower Leaf Surface: Green Group 137C. Color, juvenile foliage: Upper Leaf Surface: Yellow-Green Group 146A. Lower Leaf Surface: Yellow-Green Group 146B.

*Leaflets*.—Size: Average size of the terminal leaflet is 65 mm (l)×40 mm (w). Shape: Elliptic. Base: Obtuse. Apex: Acute. Margins: Serrated. Surface: Upper side of leaflet: Semi-glossy. Under side of leaflet: Matte. Texture: Upper side of leaflet: Smooth. Under side of leaflet: Smooth. Color, mature foliage: Upper Leaflet Surface: Green Group 137A. Lower Leaflet Surface: Green Group 137C. Color, juvenile foliage: Upper Leaflet Surface: Green Group 137A. Lower Leaflet Surface: Green Group 138A. Anthocyanin intonation: Greyed-Purple Group 183A. Location: 80-90% of upper & lower surfaces. Arrangement: Odd, pinnate. Venation: Reticulate.

*Stipules*.—Size: 20 mm (l)×10 mm (w). Stipule color: Green Group 137C. Anthocyanin: Greyed-Purple Group 185A. Stipitate glands: Abundant numbers along margins. Texture: Smooth. Shape: Apex: Apiculate. Base: Flat.

*Petiole*.—Length: Average 20 mm. Diameter: Average 2 mm. Petiole color: Yellow-Green Group 144A. Underneath: Yellow-Green Group 144B. Anthocyanin: Greyed-Red Group 178C. Prickles: None present. Stipitate Glands: Lacking. Texture: Smooth. Strength: Strong.

*Petiole rachis*.—Length: Average 22 mm. Diameter: Average 2 mm. Color: Yellow-Green Group 144A. Prickles: A few small prickles underneath. Stipitate glands: Limited numbers of stipitate glands on margins. Texture: Smooth.

Hips/seed formation: None observed.

Winter hardiness: To date, the variety has been grown successfully in Zone 6.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

* * * * *

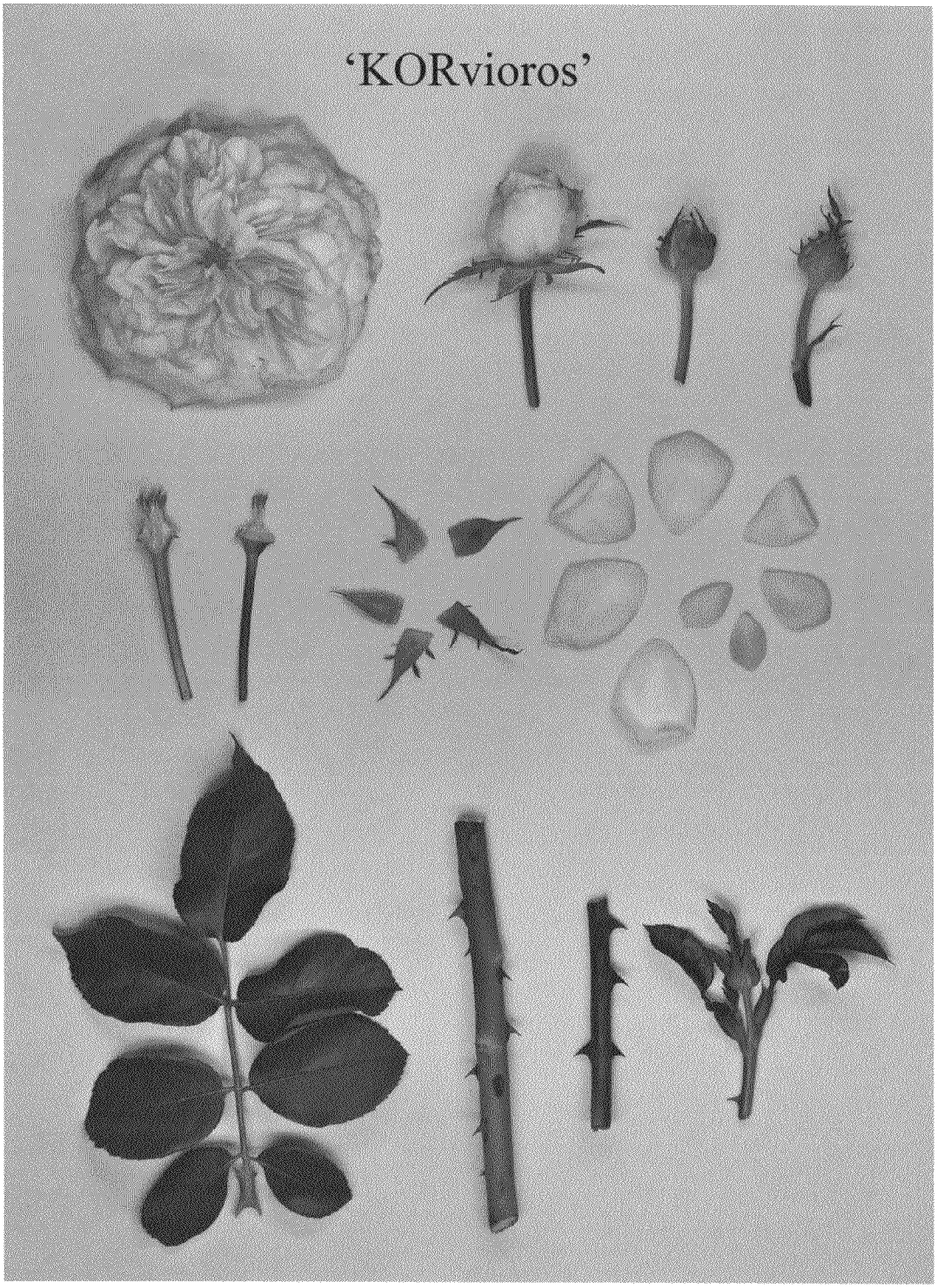
'KORvioros'